United States Patent [19]

Shorey et al.

[11] Patent Number: 5,662,914

[45] Date of Patent: Sep. 2, 1997

[54] METHODS AND COMPOSITIONS FOR REPELLING ANTS, WASPS AND TERMITES WITH REPELLENTS

[75] Inventors: Harry H. Shorey, Fresno; Lyle K. Gaston, Riverside, both of Calif.

[73] Assignee: The Regents of the University of California, Oakland, Calif.

[21] Appl. No.: 274,736

[22] Filed: Jul. 18, 1994

Related U.S. Application Data

[63] Continuation of Ser. No. 939,897, Sep. 4, 1992, abandoned.

[51] Int. Cl.$^6$ .......................... A01N 25/08; A01N 27/00; A01N 29/00; A01N 31/02
[52] U.S. Cl. .................. 424/405; 424/411; 424/DIG. 10; 514/919; 514/552; 514/560; 514/739; 514/744; 514/762
[58] Field of Search ............................ 424/84, 403, 405, 424/411–413, 419, 420, 485, 487, DIG. 10, DIG. 11; 514/739, 919, 552, 560, 744, 762

[56] References Cited

U.S. PATENT DOCUMENTS

| | | | |
|---|---|---|---|
| 3,808,339 | 4/1974 | Bordenca | 424/325 |
| 4,219,570 | 8/1980 | Inazuka et al. | 424/343 |
| 4,775,534 | 10/1988 | Bartlett et al. | 424/410 |
| 5,109,022 | 4/1992 | Jeanne et al. | 514/552 |

FOREIGN PATENT DOCUMENTS

| | | | |
|---|---|---|---|
| 130369 | 10/1979 | Japan | 424/419 |
| 0103841 | 6/1982 | Japan | 424/411 |
| 9210002 | 11/1984 | Japan | 424/487 |

OTHER PUBLICATIONS

Chem. Abstract vol. 108, 1988 #108135k Howard et al. Toxicity of Terpenoid Deterrent to the Leafcutting Ant *Atta cephalotes* & its Mutualistic fungi.
Chem. Abstract vol. 101, 1984 #1015259g Free et al. J. Apic. Res. 1983 22(9) 214–23 Effect of honeybee Nasonov & Alarm Pheromone component S on behavior at nest entrance.
Holldobler, B., et al., "Communication in Social Hymenoptera" in How Animals Communicate, Sebeok, Editor, Indiana University Press, Bloomington, Indiana, pp. 418–471 (1977).
Butenandt, et al., "Ueber Einen Duftstoff Aus Der Mandibeldruese der Blattschneiderameise *Atta sexdens Rubropilosa*," Forel. Arch. Anat. Microscop. Morph. Exp., 48:13–19 (1959).
Blum, et al., "Alkanes and Terpenes in the Mandibular Glands of Atta species," Comp. Biochem. Physiol., 26:291–299 (1968).

Schildknecht, H., "Chemical Ecology –a Chapter of Modern Natural Products Chemistry," Angew. Chem. Int. Ed. Eng., 151:214–222 (1976).
Lloyd, et al., "Chemistry of Mandibular and Dufour's Gland Secretions of Ants in Genus Myrmecocytus," J. Chem. Ecol., 15:2589–2599 (1989).
Honda, "Defensive Potential of Components of the Larval Osmeterial Secretion of Papilionid Caterpillars Against Ants," Physiol. Entomol., 8:173–179 (1983).
Scheffrahn, et al., "4,11–Epoxy–cis–Eudesmane, Soldier Cephalic Secretion of the Nearctic Desert Termite, *Amitermes minimus* Light (Termitidae: Termitinae)," Experienta, 40:1136–1137 (1984).
Post, et al., "Colony Defense Against Ants by *Polistes fuscatus* (Hymenoptera:Vespidae) in Wisconsin," J. Kans. Entomol. Soc., 54:599–615 (1981).
Post, et al., "Identification of Ant Repellent Allomone Produced by Social Wasp *Polistes fuscatus* (Hymenoptera:Vespidae)," J. Chem. Ecol., 10:1799–1807 (1984).
Henderson, et al., "Response of Aphid–Tending Ants to a Repellent Produced by Wasps (Hymenoptera:Formicidae, Vespidae)," Ann. Entomol. Soc. Am., 82:515–519 (1989).
Kistner, et al., "Alarm Pheromone of *Lasius (Dendrolasius) Spathepus* (Hymenoptera:Formici–dae) and its Possible Mimicry by Two Species of Pella (Coleoptera:Staphylinidae)," Ann. Entomol. Soc. Amer., 64:589–594 (1971).
Huth, et al., "Defense Chemicals from Abdominal Glands of Thirteen Rove Beetle Species of the Subtribe Staphylina (Coleoptera:Staph–ylinidae:Staphylininae)," J. Chem. Ecol., 16:2691–2711 (1990).
Maschwitz, "Gefahrenalarmstoffe and Gefahrenalarmierung Bei Sozialen Hymenoptera," Z. Vergl. Physiol., 47:569–655 (1964).
Scheffrahn et al., "Defensive Ecology of *Forelius foetidus* and its Chemosystematic Relationship to F. (=*Iridomyrmex*) *pruinosus* (Hymenoptera:Formicidae:Dolichoderinae)," Environ. Entomol., 13:1502–1506 (1984).
Key, et al., "Effects of Gaster Extract Trail Concentration on Trail Following Behavior in the Argentine Ant, *Iridomyrmex humilis*," J. Insect Physiol., 27:363–370 (1981).
Das, et al., "Non–Repellency of Two Insect Growth Regulators With Juvenile Hormone Activity to *Blattella germanica*," Entomol. Exp. Appl. 20(2):195–198 (1976).
Corey, et al., J. Am. Chem. Soc., 92:6637 et seq. (1970).

*Primary Examiner*—Neil S. Levy
*Attorney, Agent, or Firm*—Burns, Doane, Swecker & Mathis L.L.P.

[57] ABSTRACT

Disclosed are methods and compositions for retarding the movement of ants, wasps, and/or termites to a specific locus by use of farnesol or a farnesol related compound.

24 Claims, No Drawings

METHODS AND COMPOSITIONS FOR REPELLING ANTS, WASPS AND TERMITES WITH REPELLENTS

This application is a continuation of application Ser. No. 07/939,897, filed Sep. 4, 1992, now abandoned.

BACKGROUND OF THE INVENTION

1. Field of the Invention

This invention is directed to methods and compositions for retarding the movement of ants, wasps and/or termites to a specific locus by use of a repellent. Specifically, in this invention, ants, wasps and/or termites are retarded from moving to a specific site by use of farnesol or related compounds. In one embodiment, farnesol or a related compound is impregnated into a compatible matrix and the resulting matrix is used as a repellent barrier to retard the movement of ants, wasps, and/or termites to a specific locus.

2. References

The following references are cited in this application as superscript letters at the relevant portion of the application:

A Holldobler, B., et al., "Communication in Social Hymenoptera" in "How Animals Communicate", Sebeok, Editor, Indiana University Press, Bloomington, Ind., pp. 418–471 (1977)

B Butenandt, et al., Ueber Einen Duftstoff Aus Der Mandibeldruese der Blattschneiderameise *Atta sexdens Rubropilosa*, Forel. Arch. Anat. Microscop. Morph. Exp., 48:13–19 (1959)

C Blum, et al., "Alkanes and Terpenes in the Mandibular Glands of Atta species", Comp. Biochem. Physiol., 26:291–299 (1968)

D Schildknecht, H., "Chemical Ecology—a Chapter of Modern Natural Products Chemistry", Angew. Chem. Int. Ed. Eng., 151:214–222 (1976)

E Lloyd, et al., "Chemistry of Mandibular and Dufour's Gland Secretions of Ants in Genus Myrmecocystus", J. Chem. Ecol., 15:2589–2599 (1989)

F Honda, "Defensive Potential of Components of the Larval Osmeterial Secretion of Papilionid Caterpillars Against Ants", Physiol. Entomol., 8:173–179 (1983)

G Scheffrahn, et al., "4,11-Epoxy-cis-Eudesmane, Soldier Cephalic Secretion of the Nearctic Desert Termite, *Amitermes minimus* Light (Termitidae: Termitinae), Experienta, 40:1136–1137 (1984)

H Post, et al., "Colony Defense Against Ants by *Polistes Fuscatus* (Hymenoptera:Vespidae) in Wisconsin", J. Kans. Entomol. Soc., 54:599–615 (1981)

I Post, et al., "Identification of Ant Repellent Allomone Produced by Social Wasp *Polistes Fuscatus* (Hymenoptera:Vespidae)", J. Chem. Ecol., 10:1799–1807 (1984)

J Henderson, et al., "Response of Aphid-Tending Ants to a Repellent Produced by Wasps (Hymenoptera:Formicidae, Vespidae), Ann. Entomol. Soc. Am., 82:515–519 (1989)

K Kistner, et al., "Alarm Pheromone of *Lasius* (*Dendrolasius*) *Spathepus* (Hymenoptera:Formicidae) and its Possible Mimicry by Two Species of Pella (Coleoptera:Staphylinidae)", Ann. Entomol. Soc. Amer., 64:589–594 (1971)

L Huth, et al., "Defense Chemicals from Abdominal Glands of Thirteen Rove Beetle Species of the Subtribe Staphylina (Coleoptera:Staphylinidae:Staphylininae)", J. Chem. Ecol., 16:2691–2711 (1990)

M Maschwitz, "Gefahrenalarmstoffe and Gefahrenalarmierung Bei Sozialen Hymenoptera", Z. Vergl. Physiol., 47:569–655 (1964)

N Scheffrahn et al., "Defensive Ecology of *Forelius Foetidus* and its Chemosystematic Relationship to F. (=*Iridomyrmex*) *pruinosus* (Hymenoptera:Formicidae:Dolichoderinae)", Environ. Entomol., 13:1502–1506 (1984)

O Key, et al., "Effects of Gaster Extract Trail Concentration on Trail Following Behavior in the Argentine Ant, *Iridomyrmex humilis*", J. Insect Physiol., 27:363–370 (1981)

P Das, et al., "Non-Repellency of Two Insect Growth Regulators With Juvenile Hormone Activity to Blattella Germanica", Entomol. Exp. Appl., 20(2):195–198 (1976)

Q Stirrup-M™ available from Fermone Inc., Glendale, Ariz.

R Corey, et al., J. Am. Chem. Soc., 92:6637 et seq. (1970)

All publications mentioned in this specification are indicative of the level of skill of those skilled in the art to which this invention pertains. All publications are herein incorporated by reference in their entirety to the same extent as if each individual publication was specifically and individually indicated to be incorporated by reference in its entirety.

State of the Art

The art is continuously searching for effective and relatively safe methods for retarding the movement of ants, wasps and termites into a specific locus such as homes, trees, yards, etc. In general, ants, wasps, and/or termites are typically removed from a specific locus with an insecticide which is toxic to the ants, wasps, and/or termites. However, such use of insecticides is temporary and sometime thereafter the ants, wasps, and/or termites may reinfest the locus. Additionally, the use of insecticides causes several major concerns. Initially, the use of insecticides poses environmental concerns and indiscriminate use of such insecticides on cultivated acreage can result in contamination of agricultural products, possible contamination of ground water, etc.; whereas the indiscriminate use of insecticides in a household setting can result in contamination of food stuffs with the insecticide as well as possible exposure of the occupants to high concentrations of insecticide. Secondly, insecticides typically do not discriminate between ants, wasps, and termites and useful insects which might be exposed to the insecticide. For example, in an orchard setting, the use of such insecticides can result in removal of insects, i.e., bees which are required to pollinate the blossoms.

One alternative approach to the use of insecticides for controlling certain insects is the use of attractants or repellents. In this regard, it is well known that many social insects (e.g., ants, wasps, termites, and the like) communicate with others of their species and with their environment largely through behaviorally active chemicals[A]. Some of the chemicals cause repellency or inhibition of ongoing behavior and others cause attraction.

In regard to the above, alarm compounds released from an ant which is injured or attacked may cause a variety of specific behaviors, including repellency, in nearby ants of the same species.

The alarm compounds of some ants have received considerable study. An example is the genus Atta in which the mandibular glands contain a rich medley of chemicals including citral[B], nerol[C], geraniol[C], β-pinene[D], citral[D], farnesol[D] and 14 other compounds[D].

Another example of a chemical medley constituting ant alarm compounds was identified by Lloyd et al.[E] who found methyl salicylate to be a principal alarm component produced by workers of several species of honey ants, Myrmecocystus spp. A number of terpenoids were also found in these worker ants, including neral, geranial, citronellol, and limonene and presumably, these also possess alarm activity.

The various species of Formica, when alarmed, spray mixtures of formic acid and Dufour's gland secretion toward the enemy, with the mixtures serving simultaneously as defensive substances and alarm compounds[M].

The ant, *Forelius foetidus*, secretes 2-heptanone which, when used singly, functions as an alarm compound. It also secretes cis,trans-iridodial, which, when mixed with 2-heptanone, elicits defensive behavior in *Forelius foetidus* and repellent behavior in two other ants, *Solenopsis maniosa* and *Crematogaster californica*[N].

On the other hand, there is apparently no alarm compound released by the workers of the Argentine ant, *Iridomyrmex humilis* (Mayr)[O].

Other insects release repellents against predatory insects including ants. For example, α-pinene is released in the secretion of the larval osmeteria of papilionid caterpillars to ward off ants[F]; 4,11-epoxy-cis-eudesmane is released by the Neartic desert termite, *Amitermes minimus*, to repel the ant *Crematogaster californica*[G]; the tropical social wasps, *Polistes fuscatus*, secrete methyl palmitate into their nest supports to prevent ants of several species from preying on their brood[H,I,J]; when necessary, staphylinid beetles of the genus Pella release citronellal to disperse ants of the species *Lasius spathepus* in addition to releasing iridoid dialdehyde, α-pinene, neral, geranial, nerol, and citronellol[K,L].

In insect management, attractants are typically employed in combination with a trap which can optionally include an insecticide. In this embodiment, the insects are induced to move to the trap by the attractant and once there are trapped within and, when an insecticide is used, the insects are killed by the insecticide.

On the other hand, repellents are typically employed in solution (e.g., an aqueous solution) or are incorporated into a matrix. When incorporated into a matrix, the resulting matrix is positioned so as to form a barrier between the insects and a specific site where the insects are not to enter.

The use of repellents for agricultural and/or household insect management provides several advantages over the use of insecticides. First, because of their natural activity, the repellent is very efficient in repelling insects from a specific site. Second, the high activity of the repellent can permit the use of significantly lower concentrations of active ingredient as compared to insecticides and, in some cases, less than 20 grams per acre are required to effect repellency. In turn, when used at less than 20 grams per acre, the EPA registration guidelines for acceptance of the repellent become more feasible.

However, notwithstanding the above, one problem heretofore encountered with the use of matrices containing a repellent is that over a relatively short period of time, the repellent can lose substantial activity. The reasons for this rapid loss of repellent activity is not known with certainty but it is possible that it can relate to high volatility of the repellent, oxidation of the repellent, etc. or combinations of these reasons.

In any event, the rapid loss of activity causes several problems. Initially, when activity is rapidly lost, it is not feasible to incorporate the repellent into the matrix at the time of manufacture. Rather, it is necessary to add the repellent to the matrix at or shortly before positioning the matrix at the intended site. Secondly, even if the repellent is incorporated into the matrix at the time the matrix is positioned at its intended site, the matrix will need repeated replacements in order to effect continued insect repellency from the intended site. In any event, the entire process of impregnating the matrix, positioning the matrix and repeating this process several times becomes rather labor intensive.

In view of the above, a matrix impregnated with a repellent having prolonged repellent activity would represent a significant advance in the use of repellents in insect management.

This invention is directed to the discovery that farnesol type compounds are useful in repelling ants, wasps, and termites and is further directed to the discovery that these compounds unexpectedly provide for prolonged activity when incorporated into a matrix.

In regard to the above, it is noted that while farnesol has been disclosed as a repellent for the German cockroach, *Blattella germanica*,[P] it is also noted that a mixture containing farnesol is commercially sold as an attractant for mites[Q]. However, there appears to be no disclosure that farnesol type compounds would be an effective repellent for ants, wasps and termites or that, when combined with a compatible matrix, these compounds would provide for prolonged repellency to ants, wasps, and termites.

SUMMARY OF THE INVENTION

As noted above, this invention is directed, in part, to the discovery that farnesol and related compounds (e.g., nerolidol) are effective repellents to ants, wasps and termites. This invention is further directed, in part, to the discovery that when farnesol, compounds related to farnesol, or mixtures thereof, are incorporated into a compatible matrix, the resulting matrix possesses significantly prolonged repellent effectiveness.

In view of the above, in one of its method aspects, this invention is directed to a method for retarding ants, wasps, and/or termites from moving to a specific locus which comprises applying a repellent effective amount of a compound of formula I or of formula II:

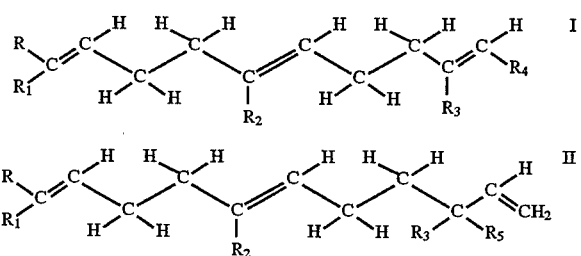

between the ants, wasps, and/or termites and the locus wherein R, $R_1$, $R_2$ and $R_3$ are independently selected from the group consisting of hydrogen and lower alkyl of 1 to 3 carbon atoms, $R_4$ is selected from the group consisting of —$CH_3$, —$CH_2OH$, —$CH_2Cl$, —$CH_2Br$, —$CH_2OC(O)R_6$, and —$COOR_7$ wherein $R_6$ is hydrogen or alkyl of from 1 to 4 carbon atoms and $R_7$ is hydrogen, alkyl of from 1 to 4 carbon atoms; and $R_5$ is selected from the group consisting of hydrogen, hydroxyl, chloro, bromo, and —$OC(O)R_6$ wherein $R_6$ is hydrogen or alkyl of from 1 to 4 carbon atoms.

In another of its method aspects, this invention is directed to a method for the prolonged retardation of ant and/or termite movement to a specific locus which comprises the steps of:

(a) impregnating a compatible matrix with a repellent effective amount of a compound of formula I or of formula II:

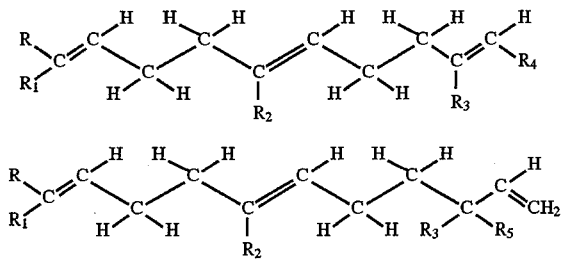

wherein R, $R_1$, $R_2$ and $R_3$ are independently selected from the group consisting of hydrogen and lower alkyl of 1 to 3 carbon atoms, $R_4$ is selected from the group consisting of —$CH_3$, —$CH_2OH$, —$CH_2Cl$, —$CH_2Br$, —$CH_2OC(O)R_6$, and —$COOR_7$ wherein $R_6$ is hydrogen or alkyl of from 1 to 4 carbon atoms and $R_7$ is hydrogen, alkyl of from 1 to 4 carbon atoms; and $R_5$ is selected from the group consisting of hydrogen, hydroxyl, chloro, bromo, and —$OC(O)R_6$ wherein $R_6$ is hydrogen or alkyl of from 1 to 4 carbon atoms;

(b) positioning the compatible matrix formed in step (a) above between said locus and said ants, wasps, and/or termites; and (c) retaining said matrix in said position for a period of at least 28 days.

In one of its composition aspects, the present invention is directed to a liquid composition comprising:

(a) a compatible matrix;

(b) a repellent effective amount of a compound of formula I or of formula II:

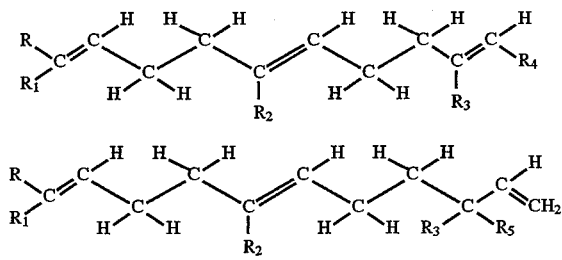

wherein R, $R_1$, $R_2$ and $R_3$ are independently selected from the group consisting of hydrogen and lower alkyl of 1 to 3 carbon atoms, $R_4$ is selected from the group consisting of —$CH_3$, —$CH_2OH$, —$CH_2Cl$, —$CH_2Br$, —$CH_2OC(O)R_6$, and —$COOR_7$ wherein $R_6$ is hydrogen or alkyl of from 1 to 4 carbon atoms and $R_7$ is hydrogen, alkyl of from 1 to 4 carbon atoms; and $R_5$ is selected from the group consisting of hydrogen, hydroxyl, chloro, bromo, and —$OC(O)R_6$ wherein $R_6$ is hydrogen or alkyl of from 1 to 4 carbon atoms; and (c) a compatible solvent.

In another of its composition aspects, the present invention is directed to a composition comprising a compatible matrix containing a repellent effective amount of a compound of formula II:

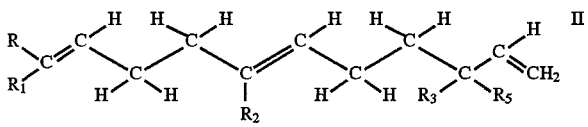

wherein R, $R_1$, $R_2$ and $R_3$ are independently selected from the group consisting of hydrogen and lower alkyl of 1 to 3 carbon atoms, and $R_5$ is selected from the group consisting of hydrogen, hydroxyl, chloro, bromo, and —$OC(O)R_6$ wherein $R_6$ is hydrogen or alkyl of from 1 to 4 carbon atoms and $R_7$ is hydrogen, alkyl of from 1 to 4 carbon atoms.

In a preferred embodiment, in the compounds of formula I, R, $R_1$, $R_2$ and $R_3$ are methyl and $R_4$ is —$CH_2OH$ (i.e., farnesol). In another preferred embodiment, in the compounds of formula II, R, $R_1$, $R_2$, and $R_3$ are methyl and $R_5$ is hydroxyl (i.e., nerolidol).

In still another preferred embodiment, the compounds of formula I and formula II are employed to retard the movement of ants and particularly Argentine ants, *Iridomyrmex humilis*.

DETAILED DESCRIPTION OF THE PREFERRED EMBODIMENTS

This invention is directed to methods and compositions for disrupting the movement of ants, wasps, and/or termites to a specific locus. The methods are achieved by the use of farnesol related compounds, i.e., the compounds of formula I and II. In a preferred embodiment, a compound of formula I or of formula II or a mixture of compounds of formula I and/or formula II are combined into a compatible matrix. However, prior to discussing this invention in further detail, the following terms will first be defined.

Definitions

As used herein, the following terms have the following meanings:

The terms "ant" and "wasp" refers to the ant and wasp members of the order Hymenoptera and include, by way of example only, the species *Iridomyrmex humilis*, *Solenopsis xyloni*, Formica spp. (ants), *Vespa vulgaris* (wasps) and the like.

The term "termite" refers to the termite members of the order Isoptera and include, by way of example only, the species *Reticulitermes hesperus*, *Zootermopsis augusticollis*, *Kalotermes minor*, and the like.

The term "locus" refers to any site to which movement of ants, wasps, and/or termites is to be retarded. The particular site is not critical and includes, by way of example, the interior of a home, a particular area of land, trees (e.g., citrus trees), and the like.

For example, it is well known that ants are a serious pest of a number of agricultural crops. The deleterious action of the ants can be direct (i.e., leaf cutting ants) or indirect. The indirect deleterious action of ants occurs, for example, in that certain species tend homopterous honey-dew-producing insects such as aphids, soft scales, and mealybugs. Through their transporting of these homopterous insects to new growth on the plants, and through their role in warding off potential parasites and predators, ants may create situations where the tended insects assume serious pest status, whereas, in the absence of ants, the insects would often be regulated through the action of beneficial predatory and parasitic species. One particular agricultural crop where ants are a serious pest are citrus trees where the ants move from the ground up to the tree to the leaves where they tend homopterous honey-dew-producing insects. Thus, in this situation, the locus for preventing movement of the ants would be the tree itself.

In another example, the locus would be the interior of a house where movement of ants, wasps, and/or termites from the outside into the home's interior is desirably retarded.

In any event, the locus is a variable which is fixed solely by that site where retardation of ant movement is desired.

The term "compatible matrix" refers to any material in which one or more of the farnesol related compounds of formula I and formula II are either soluble or miscible and which materials do not significantly alter or degrade the repellent activity of these compounds to ants, wasps, and/or termites over a period of at least 7 days and preferably at least 28 days and more preferably at least 60 days.

Suitable compatible matrices are known in the art and include, by way of example, polymeric materials such as polyethylenes, polyvinyls including Tygon™, polyisoprene such as rubber, polypropylenes, copolymers of ethylene and propylene; polybutenes such as Stickem Special™ (a polybutene based composition commercially available from Seabright Enterprises, Emeryville, Calif.), polysaccharides such as cotton twine; Tanglefoot™ (a compatible matrix which is commercially available from The Tanglefoot Company, Grand Rapids, Mich.), floor wax, and the like. Combinations of compatible matrices can be employed (i.e., cotton twine and Tanglefoot™). The particular compatible matrix employed with the farnesol related compound is not critical.

In one preferred embodiment, the compatible matrix is combined with the farnesol related compound of formula I or formula II into a volatile compatible solvent. The compatible solvent acts to solubilize the compatible matrix and the farnesol related compound. Upon application of this solution to its intended site, the volatile solvent evaporates leaving a matrix containing farnesol impregnated thereon. This embodiment permits the facile application of a film of matrix containing farnesol over a desired site.

Compatible solvents are those in which the farnesol related compound and the compatible matrix are soluble to at least 10 milligrams per milliliter of solvent and which do not significantly degrade the activity of the farnesol related compound. Volatile compatible solvents are those having a boiling point of 100° C. or less at atmospheric pressure and include, by way of example, acetone, ethanol, methanol, isopropanol, saturated hydrocarbons such as hexane, cyclohexane, aromatic compounds such as xylene, toluene, etc., and the like.

Farnesol Related Compounds

The farnesol related compounds employed herein are preferably those depicted by formula I and II above and include farnesol (i.e., in formula I, R, $R_1$, $R_2$, and $R_3$ are —$CH_3$; and $R_4$=—$CH_2OH$), nerolidol (i.e., in formula II, R, $R_1$, $R_2$ and $R_3$=—$CH_3$ and $R_5$=—OH) and compounds related thereto including congeners of farnesol and nerolidol as well other geometric isomers. Farnesol and nerolidol are well known compounds which can be isolated from natural sources. Farnesol and nerolidol are also commercially available (e.g., Aldrich Chemical Company, Milwaukee, Wis.). Moreover, the synthesis of these compounds is known in the art which includes a synthesis of farnesol disclosed by Corey et al[R].

Similarly, the other compounds described in formula I and formula II above can be readily synthesized by well known techniques. For example, derivatives of farnesol and nerolidol wherein one or more of R, $R_1$, $R_2$ and $R_3$ groups are hydrogen or lower alkyl of from 1 to 3 carbon atoms but where R, $R_1$, $R_2$, and $R_3$ are not all —$CH_3$ can be readily prepared following art known synthetic procedures by merely substituting the appropriate starting materials in such syntheses.

Likewise, farnesol derivatives wherein $R_4$ is —$CH_2OC(O)R_6$ and nerolidol derivatives where $R_5$ is —$OC(O)R_6$ are readily prepared by reacting farnesol type compounds (i.e., compounds of formula I which terminate in a $R_4$ group equal to —$CH_2OH$) and nerolidol type compounds (i.e., compounds of formula II which contain an $R_5$ group equal to —OH) with a suitable carboxylic acid, acid halide, acid anhydride or activated ester under acylating conditions well known to the skilled artisan. For example, reaction of farnesol or nerolidol with acetyl chloride [$CH_3C(O)Cl$] preferably in the presence of a tertiary amine which scavenges the acid generated during reaction leads to the corresponding ester (i.e., $R_4$ is —$CH_2OC(O)CH_3$ in farnesol and $R_5$ is —$OC(O)CH_3$ in nerolidol).

The deoxy derivatives of farnesol (i.e., $R_4$=—$CH_3$) and nerolidol (i.e., $R_5$=H) and the halo derivatives thereof (i.e., $R_4$=—$CH_2Cl$ and —$CH_2Br$; and $R_5$=—Cl and —Br) are also readily accomplished by art recognized procedures. For example, the preparation of the halo derivatives can be achieved by reaction of farnesol type compounds or nerolidol type compounds with thionyl chloride or thionyl bromide. The bromo derivative can be reduced to the deoxy derivative by reaction with, for example, lithium aluminum hydride.

Lastly, the preparation of carboxylic acid and ester derivatives of farnesol type compounds (i.e., $R_4$=—$CO_2R_6$) is also accomplished by art recognized procedures starting with farnesol type compounds (i.e., $R_4$=—$CH_2OH$). For example, the primary alcohol can be oxidized under mild conditions, for example, cold chromic acid followed by silver oxide oxidation of the aldehyde to provide for the acid (i.e., $R_4$=—$CO_2H$) which optionally can then be esterified by art recognized procedures using a $C_1$ to a $C_3$ alcohol.

Farnesol and nerolidol are preferred compounds for use herein because they are produced in nature and are known to be comparably non-toxic.

Methodology

The methodology for using a farnesol related compound of formula I or II as an ant and/or termite repellent is generally accomplished by placing a repellent effective amount of such a compound or a mixture of such compounds between the ants, wasps, and/or termites and the locus where one desires to retard movement therein of the ants, wasps, and/or termites.

The method of application is not critical and many well known methods can be used. For example, appropriate amounts of a farnesol related compound of formula I or II can be dissolved into an appropriate compatible solvent and dispensed as a solution onto the intended locus. Preferably, the solvent employed is a volatile solvent (i.e., has a boiling point of about 100° C. or less) that will evaporate over a period of time. Alternatively, a farnesol related compound can be combined with an appropriate propellant and used as a spray for application onto the intended locus.

In another embodiment, a farnesol related compound is impregnated into a compatible matrix and the matrix is then employed as a barrier layer between the ants, wasps, and/or termites and the locus from which one desires to retard ant, wasp, and/or termite movement therein. Impregnation of the farnesol related compound into the compatible matrix can be achieved by any well known methods known in the art. For example, the farnesol related compound can be dissolved into a compatible volatile solvent and the resulting solution added to the matrix whereupon evaporation of the solvent results in impregnation of the farnesol related compound into the compatible matrix. In this regard, the matrix can be cotton twine, polymers such as polyvinyls (such as Tygon™), polyisoprenes (such as rubber), polyethylene, polypropylene or copolymers thereof, polybutenes (such as Stickem™), etc., Tanglefoot™, and the like. In another embodiment, a compatible matrix such as Tree Tanglefoot™ is thinned by heating and then the farnesol related compound is added directly thereto. The mixture can then be combined with twine or other compatible matrices. The resulting combination is then applied around the selected locus to form a barrier which retards movement of ants, wasps, and/or termites there past.

One example of this mode of application is the incorporation of a farnesol related compound into a floor wax composition such as those which are readily commercially available. Upon application of the floor wax and removal of any volatile solvent, the resulting wax will contain farnesol. Another example of this mode of application is the impregnation of a farnesol related compound into a compatible matrix such as Tygon™, rubber, Stickem™, or Tanglefoot™. The resulting matrix is then banded around the locus from which ants, wasps, and/or termites are to be retarded (e.g., the trunk of a tree or the wall of a house).

Regardless of the method of application, the amount of the farnesol related compound used is a repellent effective amount. That is to say that sufficient amounts of the farnesol related compound or mixture of compounds is used so as to retard the movement of ants, wasps, and/or termites to the selected locus. In a preferred embodiment, the farnesol related compound is applied at a rate of at least about 0.05 milligrams per square foot and more preferably at a rate of about 0.5 milligrams per square foot to about 5 grams per square foot. In another embodiment, the application rate of the farnesol related compound is about 20 grams per acre or less. When used at this rate, the EPA registration for the use of this compound is simplified.

When employed to retard movement of ants (e.g., Argentine ants) into trees, the farnesol related compound of formula I or II is preferably incorporated into Stickem™ which is then banded around tree trunks. About 0.008 to about 2 grams of a farnesol related compound is preferably employed per tree trunk having a diameter of from about 3 to about 5 centimeters.

In another embodiment, ants, wasps, and/or termites are removed from the locus prior to application of the farnesol related compound. Removal can be achieved by conventional methods such as by using an insecticide. After removal, the farnesol related compound retards reinfestation of the locus by ants, wasps, and/or termites.

In a preferred embodiment, effective retardation of ant, wasp, and/or termite movement is accomplished when movement into the locus is reduced by at least 50% and preferably by at least 80% and more preferably by at least 95% as compared to control.

In addition to retarding movement of ants, wasps, and/or termites, the farnesol related compounds disclosed herein are effective in retarding the movement of other insects and arachnida such as spiders, fleas, ticks, etc. Accordingly, in another embodiment, a repellent effective amount of a farnesol related compound can be formulated into a matrix suitable for use in retarding flea infestation of pets.

The following examples are offered to illustrate this invention and should not be construed in any way as limiting its scope.

EXAMPLES

General Procedures

The examples set forth below were conducted in a planting of young, non-bearing lemon trees. The trees were about 2 meters high and the stem diameter ranged from 3 to 5 centimeters at 10 centimeters above the soil surface. The trees were heavily infested with a variety of honey-dew-producing Homoptera, and the Argentine ants made trails from their nests in the ground, up the trunks to the vicinities of the insects they were tending.

A double layer of duct tape was wrapped around the trunks of the trees, at about 10 centimeters above the soil surface. Candidate chemicals tested for disrupting ant trail following (i.e., retarding ant movement) were placed on specified lengths of cotton twine or Tygon™ or rubber tubing, which were then wrapped two or three times around the tree trunk, over the duct tape. The tape was intended to protect the tree trunk from possible phytotoxic effects of the tested chemicals. Under most circumstances, the twine or tubing was held in position by staples driven through the duct tape and into the tree trunk. An exception to this procedure occurred in the case of Stickem™ or Tree-Tanglefoot™ impregnated cotton twine, the ends of which were tucked under the loops of twine wrapped around the trunk.

Chemicals tested were obtained from commercial sources and are listed in Examples 1–5 below. When a given chemical was tested in conjunction with a matrix of sticky material such as Stickem Special™ (commercially available from Seabright Enterprises, Emeryville, Calif.) or Tree Tanglefoot™ (commercially available from The Tanglefoot Company, Grand Rapids, Mich.), the sticky material was first thinned through heating; the specified amount of sticky material was then mixed with the candidate chemical; finally, this sticky material-chemical mixture was placed in a glass jar containing a specified length of cotton garden twine (Puritan™ twine) and was continuously agitated until essentially all of the mixture was incorporated in and on the twine.

Efficacy of disruption of any trail-following and foraging was evaluated on specified days following placement of the chemical-impregnated twine or tubing around tree trunks, by counts of the numbers of ants walking across the twine or tubing during a 2 minute interval. Ants were counted without regard to whether they were proceeding up or down the trunk. Untreated control counts were made of ants crossing over a band of untreated twine around control tree trunks.

Example 1

Following the general procedures set forth above, nineteen chemicals were tested for efficacy through inoculation of 1 gram of each onto 30 centimeter lengths of cotton twine, which were then wrapped around the trunks of test trees. Each tree was regarded as a plot, and treatments were replicated three times in a randomized complete blocks design. Counts of ants passing over the test twine were made on the sixth day following application. The results of this test are set forth in Table I below:

TABLE I

| CHEMICAL | Mean no. ½ minutes of ants passing barrier on day 6 |
|---|---|
| farnesol | 0.0 a |
| methyl eugenol | 0.6 ab |
| β-citronellol | 0.7 abc |
| bornyl acetate | 0.9 abc |
| eugenol | 1.7 bcd |
| methyl myristate | 2.1 cde |
| citral | 4.6 def |
| methyl salicylate | 4.7 def |
| safrole | 5.4 efg |
| limonene | 5.7 efg |
| linalool | 6.1 fgh |
| benzaldehyde | 8.7 fgh |
| methyl anthranilate | 10.0 fgh |
| limonene oxide | 10.1 fgh |
| α-terpineol | 11.5 fgh |
| myrcene | 11.5 fgh |
| α-pinene | 12.5 fgh |
| β-pinene | 13.5 gh |
| 3-carene | 16.0 h |
| Untreated | 10.1 fgh |

[1]Each treatment chemical was replicated three times in a randomized complete blocks design. Counts of ants crossing the barriers in 2 minutes were transformed to ln(X + 1) for ANOVA. Duncan's Multiple Range Test was performed on transformed means. Means in the same column followed by a common letter are not significantly (5% probability) different. Means presented here are transformed back to the original scale.

The results of Table I indicate that farnesol is an excellent repellent 6 days after placement of the barrier around the tree trunk.

Example 2

Following the procedures set forth above, testing was conducted to evaluate the efficacy of methyl eugenol incorporated into 30 centimeter length of Tygon tubing of three different sizes or into 30 centimeter length of one size of latex rubber tubing, and of citral incorporated only into the rubber tubing. Approximately a 1:1 weight ratio of these chemicals to matrix were incorporated into the matrix by occasional agitation over a 24-hour period. The results of this test are set forth in Table II below:

TABLE II

| Chemical | Tubing | passing barrier on day | | |
|---|---|---|---|---|
| | | 2 | 6 | 9 |
| methyl eugenol | Tygon[2] | 2.4 ab | 0.9 ab | 2.4 abc |
| | Tygon[3] | 0.6 a | 0.7 ab | 1.5 ab |
| | Tygon[4] | 0.0 a | 0.0 a | 0.6 a |
| | Rubber[5] | 0.2 a | 0.0 a | 1.0 a |
| citral | Rubber[5] | 0.3 a | 2.7 bc | 8.2 bc |
| untreated | | 4.6 b | 7.4 c | 18.8 c |

[1]Each treatment chemical was replicated three times in a randomized complete blocks design. Counts of ants crossing the barriers in 2 minutes were transformed to ln(X + 1) for ANOVA. Duncan's Multiple Range Test was performed on transformed means. Means in the same column followed by a common letter are not significantly (5% probability) different. Means presented here are transformed back to the original scale.
[2]0.8 mm ID × 2.38 mm OD, holds 2.1 g of chemical
[3]1.59 mm ID × 4.76 mm OD, holds 5.6 g of chemical
[4]4.76 mm ID × 7.94 mm OD, holds 13.2 g of chemical
[5]6.35 mm ID × 7.94 mm OD, holds 3.0 g of chemical The above results evidence that methyl eugenol was more active in retarding the movement of Argentine ants than was citral. However, even at the heaviest application of methyl eugenol in tygon, at about 13 grams per tree, complete deterrence of ant movement was only seen for about one week.

Example 3

Some of the chemicals employed in Example 1 were mixed as either 10 or 40 weight percent solutions in Stickem™, which was then incorporated at the rate of 2 grams formulated material into 50 cm lengths of cotton twine. The treated lengths of twine were placed around tree trunks and evaluated as described above. The results of this evaluation are set forth in Table III below:

TABLE III

| Chemical | Weight Percent | Mean no. ½ minutes ants passing barrier on day | | |
|---|---|---|---|---|
| | | 3 | 7 | 14 |
| farnesol | 10 | 0.0 a | 0.9 ab | 9.9 ab |
| | 40 | 0.0 a | 0.0 a | 2.4 a |
| β-Citronellol | 10 | 5.7 b | 9.0 bcd | 9.0 ab |
| | 40 | 0.0 a | 2.7 abc | 49.8 b |
| methyl eugenol | 10 | 9.0 b | 16.2 cd | 13.3 ab |
| | 40 | 0.6 a | 4.2 abcd | 7.4 a |
| citral | 10 | 6.1 b | 14.3 cd | 26.5 ab |
| | 40 | 1.6 ab | 28.2 d | 30.2 ab |
| Stickem™ alone | | 3.2 ab | 5.5 bcd | 12.4 ab |
| untreated | | 12.5 b | 18.8 cd | 21.6 ab |

[1]Each treatment chemical was replicated three times in a randomized complete blocks design. Counts of ants crossing the barriers in 2 minutes were transformed to ln(X + 1) for ANOVA. Duncan's Multiple Range Test was performed on transformed means. Means in the same column followed by a common letter are not significantly (5% probability) different. Means presented here are transformed back to the original scale.

The above results evidence that complete retardation of ant foraging for seven days after application was accomplished with 40 weight percent farnesol treatment (giving 0.8 g farnesol per tree). By three days after application, and continuing through 14 days, farnesol exhibits the best prolonged repellency activity of the compounds tested.

Example 4

Farnesol and Stickem™ were tested at higher application rates following the general procedure set forth above. In this example, farnesol and a 1:1 mixture of farnesol:Stickem™ mixture were prepared as above and then placed onto 50-cm lengths of cotton twine, wrapped around tree trunks in the manner described above. Also tested were 30 centimeter lengths of rubber tubing, each containing 3 grams of farnesol. The results of this test are set forth in Table IV below:

TABLE IV

| Composition Applied | Mean no. ½ minutes ants passing barrier on day | | | | | |
|---|---|---|---|---|---|---|
| | 7 | 14 | 27 | 48 | 77 | 122 |
| A | 0.0 a | 0.6 a | 4.9 a | 0.0 a | 0.6 a | 4.9 a |
| B | 0.0 a | 0.0 a | 0.0 a | 0.0 a | 0.0 a | 0.0 a |
| C | 6.0 b | 1.3 a | 1.5 a | 6.0 b | 1.3 a | 1.5 a |
| D | 21.9 b | 23.0 b | 52.2 b | 21.9 b | 23.0 b | 52.2 b |

[1]Each treatment chemical was replicated three times in a randomized complete blocks design. Counts of ants crossing the barriers in 2 minutes were transformed to ln(X + 1) for ANOVA. Duncan's Multiple Range Test was performed on transformed means. Means in the same column followed by a common letter are not significantly (5% probability) different. Means presented here are transformed back to the original scale.

In this table, the composition (Comp.) applied is as follows:
A=50 cm of twine containing 2 grams of farnesol
B=50 cm of twine containing 2 grams of Stickem™+2 grams of farnesol C=30 cm of latex rubber tubing (6.35 mm ID×7.94 mm OD) containing 2 grams of farnesol
D=Untreated The results of this test indicate that farnesol alone, at 2 grams per twine per tree, provided effective (over 90% as compared to control) retardation of movement for about 4 weeks; rubber tubing containing 3 grams of farnesol per tree provided effective retardation of movement for about 7 weeks; and 2 grams of farnesol in 2 grams of Stickem™ provided effective retardation for at least 17 weeks.

Example 5

Following the general procedure set forth above, additional chemicals were tested as mixtures of Stickem™ (2 grams of chemical in 2 grams of Stickem™). These were compared for efficacy with a farnesol/Stickem™ mixture. Also tested were a farnesol/Tree Tanglefoot™ mixture, Tree Tanglefoot™ alone, and Stickem™ alone. The results of these tests are set forth in Table V below:

TABLE V

| Comp. Applied | Mean no. ½ minutes ants passing barrier on day | | | | |
|---|---|---|---|---|---|
| | 7 | 14 | 21 | 50 | 95 |
| A | 1.4 ab | 4.3 ab | 4.1 ab | | |
| B | 26.0 c | 35.6 b | 65.3 b | | |
| C | 1.8 ab | 8.7 ab | 4.8 ab | | |
| D | 1.3 a | 14.8 b | 11.5 b | | |
| E | 1.4 ab | 13.0 b | 9.8 b | | |
| F | 0.0 a | 0.0 a | 0.0 a | 0.0 a | 0.0 a |
| G | 0.0 a | 0.0 a | 0.0 a | 0.5 a | 35.5 a |
| H | 17.5 c | 11.6 b | 22.9 b | 52.7 b | 48.7 a |
| I | 1.34 bc | 24.5 b | 26.1 b | 56.5 b | 155.8 b |
| J | 27.3 c | 33.8 b | 33.8 b | 58.3 b | 135.6 b |

[1]Each treatment chemical was replicated five times in a randomized complete blocks design. Counts of ants crossing the barriers in 2 minutes were transformed to ln(X + 1) for ANOVA. Duncan's Multiple Range Test was performed on transformed means. Means in the same column followed by a common letter are not significantly (5% probability) different. Means presented here are transformed back to the original scale.

In this table, the composition (Comp.) applied is as follows:
A=Stickem™+3,6-dimethyl-4-octyne-3,6-diol
B=Stickem™+abietic acid
C=Stickem™+nerol
D=Stickem™+linalyl acetate
E=Stickem™+citral dimethyl acetate
F=Stickem™+farnesol
G=Tree Tanglefoot™+farnesol
H=Stickem™ alone
I=Tree Tanglefoot198 alone
J=Untreated The above results evidence that there is no significant difference between Stickem™ and Tree Tanglefoot™ alone in disrupting ant movement. Both materials were penetrated almost immediately (within 7 days) by significant numbers of ants. However, farnesol mixed with Tree Tanglefoot™ gave effective disruption of ant movement for 7 weeks, and farnesol mixed with Stickem™ gave effective retardation of ant movement for about 14 weeks.

Example 6

A laboratory bioassay was conducted to compare the repellency of nerolidol to farnesol in repelling the Argentine ant. This bioassay was conducted by measuring the numbers of ants crossing a barrier having nerolidol or farnesol impregnated into bees wax. Specifically, the bees wax was heated to liquid, the appropriate amount of compound was added and the solution stirred. The resulting liquid compositions was streaked into a circle around a food source (sucrose/water) and the number of ants passing the circle per unit time was measured and then compared to the untreated control (bees wax alone). The difference in the number of ants passing past the control and the test composition divided by the control and multiplied by 100 was used as a measure of percent repellency. The results are set forth in Table VI below:

TABLE VI

| Weight % of Compound | % Repellency |
|---|---|
| 1.0% Farnesol | no decrease (average of 5 runs) |
| 3.0% Farnesol | 98% (average of 5 runs) |
| 0.03% Nerolidol | 63% (average of 4 runs) |
| 0.10% Nerolidol | 73% (average of 4 runs) |
| 0.30% Nerolidol | 93% (average of 4 runs) |
| 1.0% Nerolidol | 100% (average of 4 runs) |
| 3.0% Nerolidol | 100% (average of 4 runs) |

The above results evidence that farnesol and nerolidol (a farnesol related compound) are both effective in retarding the movement of ants. These results also evidence that nerolidol is significantly more active than farnesol in retarding the movement of ants. For example, the retardation arising from the use of 0.3 weight percent nerolidol were approximately equivalent to those achieved by using 3 weight percent farnesol.

Other farnesol related compounds could be substituted for either farnesol or nerolidol in the above examples including, by way of example, farnesol derivatives such as where R, $R_1$, $R_2$ and $R_3$ are methyl and $R_4$ is —$CH_2OC(O)R_6$, —$CH_2Cl$, —$CH_2Br$, and —$CO_2H$; and nerolidol derivatives where R, $R_1$, $R_2$ and $R_3$ are methyl and $R_5$ is —$OC(O)R_6$, —Cl, —Br. Similarly, other compatible matrices could be substituted for Stickem™, Tree Tanglefoot™, cotton twine, and bees wax in the above examples.

What is claimed is:

1. A method for retarding ants, wasps, and/or termites from moving to a specific locus which comprises:

a) selecting a compound of formula I or of formula II:

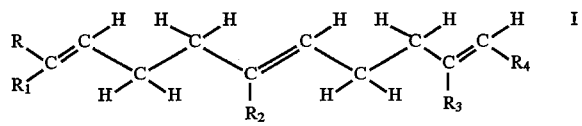

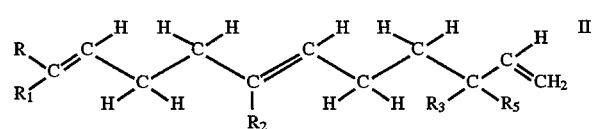

; and b) applying a non-insecticidal composition consisting essentially of a repellent effective amount of said compound and a compatible matrix between the ants, wasps, and/or termites and the locus to thereby prevent the ants, wasps and/or termites from moving to said locus wherein R, $R_1$, $R_2$ and $R_3$ are independently selected from the group consisting of hydrogen and lower alkyl of 1 to 3 carbon atoms, $R_4$ is selected from the group consisting of —$CH_3$, —$CH_2OH$, —$CH_2Cl$, —$CH_2Br$, —$CH_2OC(O)R_6$, and —COOR$_7$ wherein R$_6$ is hydrogen or alkyl of from 1 to 4 carbon atoms and R$_7$ is hydrogen, alkyl of from 1 to 4 carbon atoms, R$_5$ is selected from the group consisting of hydrogen, hydroxyl, chloro, bromo, and —OC(O)R$_6$ wherein R$_6$ is hydrogen or alkyl of from 1 to 4 carbon atoms.

2. The method according to claim 1, wherein a compound of formula I is employed.

3. The method according to claim 1, wherein a compound of formula II is employed.

4. The method according to claim 2, wherein R, R$_1$, R$_2$, and R$_3$ are methyl.

5. The method according to claim 4, wherein R$_4$ is —CH$_2$OH.

6. The method according to claim 3, wherein R, R$_1$, R$_2$, and R$_3$ are methyl.

7. The method according to claim 6, wherein R$_5$ is —OH.

8. The method according to claim 1, wherein the movement of ants is retarded.

9. The method according to claim 8, wherein the ants are Argentine army ants.

10. The method according to claim 1 wherein the locus is selected from the group consisting of the interior of a home and trees.

11. A method for retarding ants, wasps and/or termites from moving to a locus which comprises:

a) selecting a compound from the group consisting of farnesol and nerolidol;

b) applying a non-insecticidal composition consisting essentially of a repellent effective amount of said compound and a compatible matrix between the ants, wasps, and/or termites and the locus to thereby prevent the ants, wasps and/or termites from moving to said locus, wherein said locus is selected from the group consisting of the interior of homes and trees.

12. A method for the prolonged retardation of ant, wasp and/or termite movement to a specific locus which comprises the steps of:

(a) impregnating a compatible matrix with a composition consisting essentially of a non-insecticidal repellent effective amount of a compound of formula I or of formula II:

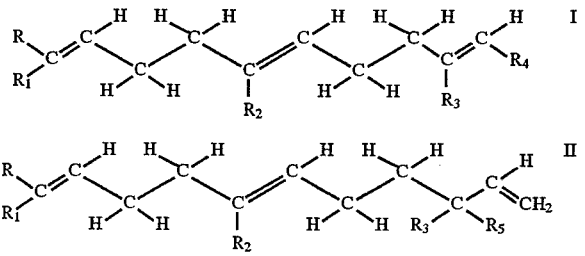

wherein R, R$_1$, R$_2$ and R$_3$ are independently selected from the group consisting of hydrogen and lower alkyl of 1 to 3 carbon atoms, R$_4$ is selected from the group consisting of —CH$_3$, —CH$_2$OH, —CH$_2$Cl, —CH$_2$Br, —CH$_2$OC(O)R$_6$, and —COOR$_7$ wherein R$_6$ is hydrogen or alkyl of from 1 to 4 carbon atoms and R$_7$ is hydrogen, alkyl of from 1 to 4 carbon atoms; and R$_5$ is selected from the group consisting of hydrogen, hydroxyl, chloro, bromo, and —OC(O)R$_6$ wherein R$_6$ is hydrogen or alkyl of from 1 to 4 carbon atoms;

(b) positioning the compatible matrix formed in step (a) above between said locus and said ants, wasps, and/or termites to thereby prevent said ants, wasps and/or termites from moving to said locus; and (c) retaining said matrix in said position for a period of at least 28 days.

13. The method according to claim 12, wherein a compound of formula I is employed.

14. The method according to claim 12, wherein a compound of formula II is employed.

15. The method according to claim 12, wherein R, R$_1$, R$_2$, and R$_3$ are methyl.

16. The method according to claim 15, wherein R$_4$ is —CH$_2$OH.

17. The method according to claim 14, wherein R, R$_1$, R$_2$, and R$_3$ are methyl.

18. The method according to claim 17, wherein R$_5$ is —OH.

19. The method according to claim 12, wherein the movement of ants is retarded.

20. The method according to claim 19, wherein the ants are Argentine army ants.

21. The method according to claim 12 wherein the locus is selected from the group consisting of the interior of a home and trees.

22. A method for the prolonged retardation of ant, wasp and/or termite movement to a specific locus which comprises the steps of:

(a) impregnating a compatible matrix with a composition consisting essentially of a non-insecticidal repellent effective amount of a compound selected from the group consisting of farnesol and nerolidol;

(b) positioning the compatible matrix formed in step (a) above between said locus and said ants, wasps, and/or termites to thereby prevent said ants, wasps and/or termites from moving to said locus; and (c) retaining said matrix in said position for a period of at least 28 days.

23. The method of claim 11 wherein the insects to be retarded are ants.

24. The method of claim 22 wherein the insects to be retarded are ants.

* * * * *